United States Patent [19]

Charton et al.

[11] Patent Number: 4,790,823

[45] Date of Patent: Dec. 13, 1988

[54] APPARATUS FOR INJECTING OR WITHDRAWING SUBSTANCES

[75] Inventors: Jean-Pierre Charton, Dijon; Gilbert Gasquet, Nangis, both of France

[73] Assignee: Societe Civile de Recherches Mesalyse, Esternay, France

[21] Appl. No.: 14,498

[22] Filed: Feb. 13, 1987

[30] Foreign Application Priority Data

Feb. 14, 1986 [FR] France .................. 86 02448

[51] Int. Cl.⁴ .................................. A61M 5/20
[52] U.S. Cl. ........................ 604/136; 604/157; 604/191
[58] Field of Search ............ 604/187, 117, 130, 211, 604/136, 137, 156, 191

[56] References Cited

U.S. PATENT DOCUMENTS

| | | | |
|---|---|---|---|
| 3,051,173 | 8/1962 | Johnson et al. | 604/156 X |
| 4,333,459 | 6/1982 | Becker | 604/117 |
| 4,475,666 | 10/1984 | Bilbrey et al. | 604/155 X |
| 4,563,175 | 1/1986 | Lafond | 604/191 X |
| 4,613,328 | 9/1986 | Boyd | 604/156 |

*Primary Examiner*—Stephen C. Pellegrino
*Attorney, Agent, or Firm*—Charles Fallow; Martin P. Hoffman; Mitchell B. Wasson

[57] ABSTRACT

The device comprises, among other things, a hand piece (10) equipped with a support (12) movable in translation for a needle (51). Support (12) is moved by a catapult which comprises a propelling device (133) made of a pneumatic microactuator with a simple spring-back effect.

Application to human mesotherapy, for example, FIG. 3.

23 Claims, 4 Drawing Sheets

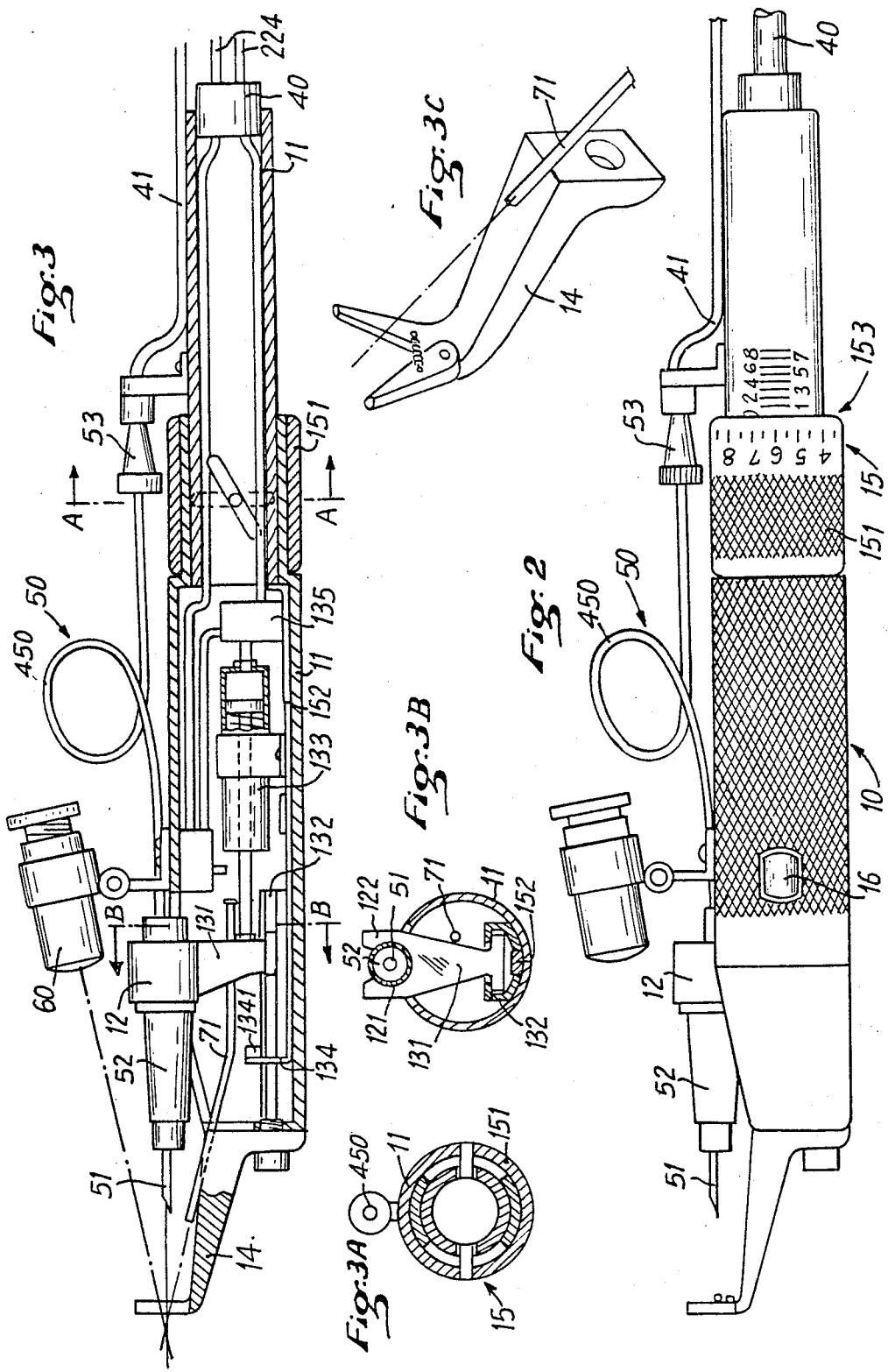

APPARATUS FOR INJECTING OR WITHDRAWING SUBSTANCES

The invention relates to injections or samples, especially for living beings or for commodities, foodstuffs, for example, and in particular a device for performing injections, especially for medicinal purposes in veterinary or medical use and, most especially, for the practice of mesotherapy in human beings.

As is known, injections are generally performed using a needle, whether or not first connected to a syringe, which is inserted into the tissues of a living being.

The injection can be intramuscular or intravenous. In certain cases, an injection in a very specific location is desired: this requires the insertion of the needle point at a well defined place and depth. This is sought in mesotherapy, where injection directly into the zone whose disease warrants treatment by medicinal injection is desired. Generally, the injection is made in the mesoderm, i.e., at a depth ranging from about some tens to several millimeters from the surface of the skin.

This injection can be made in the form of a single, constant flow or in the form of a discontinuous, multiple flow in a sequence of spurts.

Whatever the method of admininstering the medicinal substance, it is certain that precise placement of the tip of the needle in the tissues poses problems, in particular when the tip is inserted by hand, because then only the skill and dexterity of the practitioner performing the insertion guarantee a good, painless insertion.

Difficulties of the same nature arise when performing vaccinations or taking samples, where it is necessary to make punctures at very precise depths.

Another sector of activity involves foodstuffs. To prolong the time the foodstuff can be used or conserved, it is common to inject ozone or antibiotics for example, or to perform seedings.

In an attempt to remedy the difficulties connected with manual insertion of needles into living tissues, devices have already been suggested which perform such an action more or less automatically, but none of them are entirely satisfactory.

In fact, if a device which appears like a very big pistol is substituted for the hand of the operator, use is delicate: in such a case, the needle connected to a syringe is propelled by a mechanism into the epidermis of the living being and the penetration of the needle is particularly painful because the moving part is very large, due to the presence of the full syringe, causing no small problems of shock and vibrations.

For veterinary purposes, another solution for very small or very large animals consists in disconnecting the syringe from the needle and reconnecting them using a flexible connection to route the medicinal substance from the syringe to the needle in a way such that the practitioner has only to hold the needle: the needle is put by hand and the syringe itself is motorized. Whatever the advantage of this might be, the needle is still inserted manually and, if depth stops are needed to determine the distance the needle penetrates the tissues, the exact zone in which the insertion is actually made always depends on the dexterity of the practitioner.

None of these solutions is suitable for solving the difficulties mentioned and, furthermore, they are particularly painful.

The object of the invention is to remedy these inconveniences.

The object of the invention is a device for making injections or samples of substances, particularly medicinal, for example in the tissues of living beings or foodstuffs, which is light, not bulky, and very easy to handle, as well as entirely automatic and completely motorized in such a way that the insertion of the needle and the flow of the substance to be injected or taken as a sample can be done almost automatically and without pain, where living beings are concerned, regardless of the dexterity of the operator.

Furthermore, because of its design, the device according to the invention allows an insertion of the needle practically perpendicular to the surface level of the tissues as well as insertions almost tangential to these and, because of its very small relative size, it is suitable for stomatological use, which no other device known in the art allows.

The object of the invention is a device for making injections or taking samples of substances in an environment, particularly in the tissues of living beings, which comprises a hand piece intended to hold a needle to insert it in an environment, a central body equipped with a dispenser for at least one substance intended to supply the needle, a control unit connected, among other things, to the hand piece and the dispenser to make them function, and a connection which connects the hand piece to the central body and to the control unit and which is notably equipped with a duct to connect the needle to the dispenser to be able to route the substance from the dispenser to the needle or vice versa.

This device is particularly characterized in that the hand piece which comprises a lightweight support to receive a needle that is detacheable and mounted movable in translation between a rest and an active position to insert a needle, and a catapult to propel the support from its rest to its active position.

The device according to the invention, which can be used in many areas of activity, has an application especially in human mesotherapy.

Other characteristics of the invention will appear in reading the description and the claims which follow and in examining the accompanying drawings, given only as examples, where:

FIG. 2 is an exterior view of another embodiment of a hand piece according to the invention;

FIG. 3 is a partially diagrammatic longitudinal cross section of the embodiment of FIG. 2;

FIGS. 3A and 3B are cross sections of surfaces A and B with respect to FIG. 3;

FIG. 3C is a partial view in perspective of an embodiment of the end support base;

For convenience in the description, the description and the drawings will be limited to that which directly concerns the invention. Anything referring to standard techniques, such as electric, hydraulic, pneumatic, or automatic, will be mentioned only briefly because they are well known by experts in the field.

Figure 1:
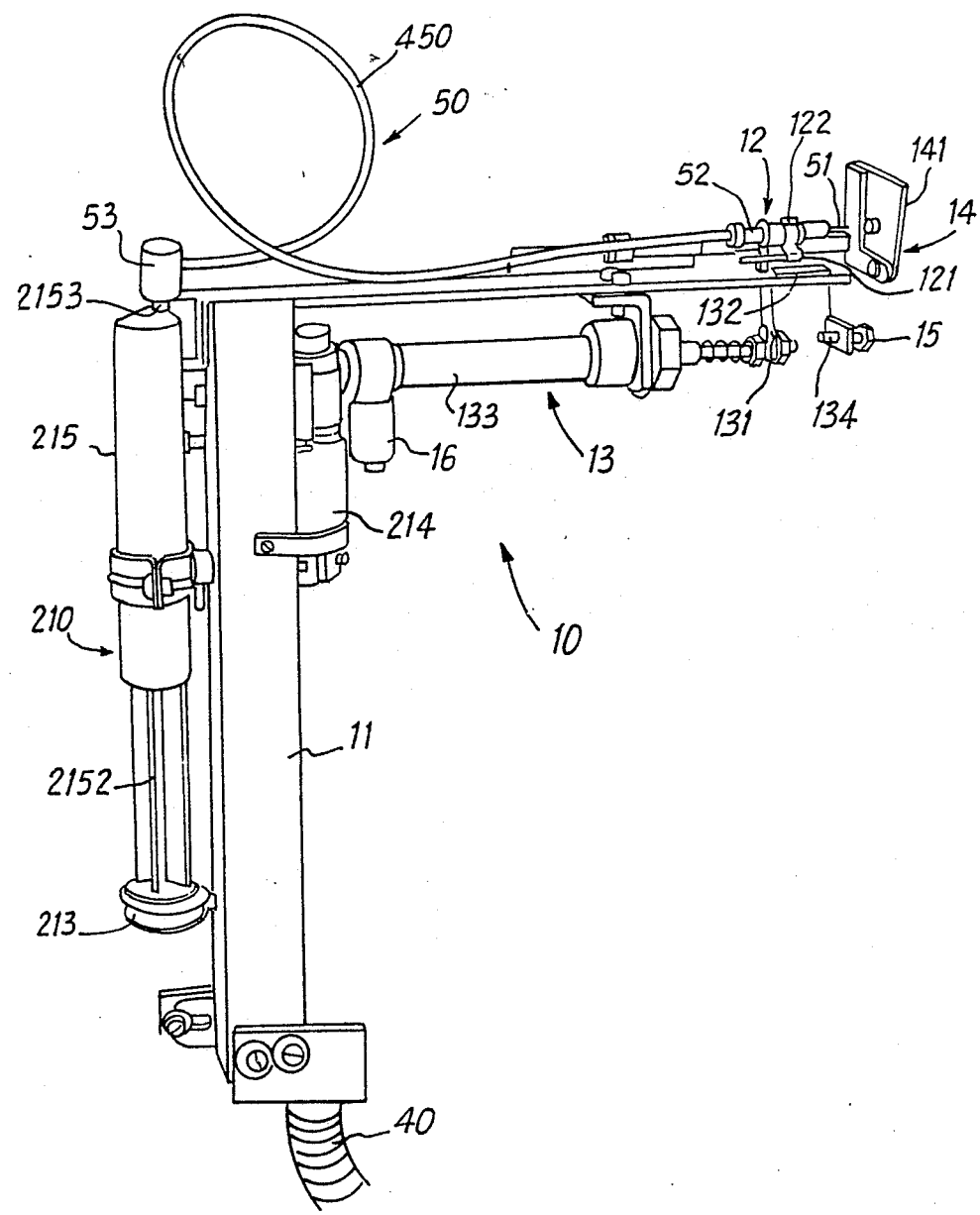
FIG. 1 is a view of an embodiment of a hand piece according to the invention.

FIG. 1 shows a first embodiment of a hand piece 10 of a device according to the invention. As can be seen, this hand piece is drawn without its protective caps which act as coverings and give it its ultimate appearance.

Hand piece 10 comprises a body 11, in the form of a bracket, on which is mounted a support 12 to receive an injector 50. This support 12 comprises a cradle 121 in which an injector lies, as indicated by the following, and a holding device 122, for example elastic clips, for keeping the injector in its cradle.

The hand piece also comprises a catapult 13 with a carriage 131 to which support 12 is attached. Carriage 131 moves in translation on a guide path 132 made, for example, of V-shaped corner iron or of standard slides, for example with adjustable balls. In that way, support 12 can move with precision in translation between a retracted rest position and an active position where the injector connected to it protrudes. The movement in translation of carriage 131 is provided by a propelling device 133, which suddenly pushes the carriage with its support from its rest position, as illustrated, to its active position. This propelling device 133 comprises, for example, a spring-back pneumatic microactuator whose cylinder is attached to body 11 and whose piston rod is connected to support 12 through carriage 131; this holding device and connection are provided by any appropriate standard technique. Instead of the actuator an electromagnet can be used, for example, operating by attraction or repulsion.

As can be seen, the active position of carriage 131 is determined by an adjustable stop 134. Positioning of this stop 134 is controlled by adjustment means 15, for example with a screw and nut of the type with a micrometer vernier, or by any other similar technique. As drawn in FIG. 3 and 3A, these adjustment means include a roller wheel 151 acting on a slide 152 through a standard slot and pin joint; a pin solid with the roller wheel simultaneously goes through a circular slot of the stationary body and a spiral slot of the mobile slide.

The stop is equipped with a damping device 1341 so that when the carriage is propelled into active position it stops without recoil against the stop, with locking if necessary to immobilize it until the end of the intervention.

A dispenser 210 of central body 20 is mounted on the other branch of body 11. This dispenser comprises a standard syringe 215, which is held in place in any appropriate manner, for example a screw clamp and whose piston 2152 is connected to a pusher 213, which is driven in translation by a screw and nut mechanism, for example, using, for example, a reversible stepper micrometer 214 whose number of rotations and speed can be varied; the speed of translation of the piston of the syringe and the distance it moves can thus be modified to cause the desired amount of medicinal substance to come out of the syringe at the required speed, according to its type and administration.

Injector 50 comprises a needle 51 set in a mounting 52 made, for example, of molded plastic material, and an adapter 53 for the reasons indicated below. As needed, the mounting and the adapter are connected by a duct section 450, for example a microcatheter.

Mounting 52 of needle 51 is held on cradle 121 of support 12 by any appropriate technique, for example a circlip or a clip. Adapter 53 is intended to be connected to a single or multiple channel duct 41 of connection 40, which will be discussed later and which, in this embodiment, is reduced to its extreme limit.

In this way, for every patient or intervention, for well known reasons involving disinfecting and sterilizing, the needle can be changed easily and rapidly by replacing the injector. If necessary, only needle 51 set in its mounting 52 is removable without having to attach to it duct section 450 for a single usage.

One end of hand piece 10, next to support 12 of the injector, is equipped with support base 14, for example a claw in the form of a bracket, one of whose forked branches is divided into a V shape. The two teeth of the fork are intended to be supported by the environment, for example the epidermis of the tissues of a patient, in such a way as to determine the relative position of the device according to the invention with regard to the area showing a pathology to be treated in this case. The V-shaped configuration of the claw furthermore allows it to stretch the tissues between its teeth, which offers other advantages as will be seen later. If necessary, to avoid the inconveniences produced by the formation of a protruding "cushion" resulting from the application of the support base against the epidermis, the two teeth of the fork are articulated like scissors handles, which normally lie close to one another when closed. These neighboring handles separate due to the action of an appropriate mechanism, which can be disengaged at will if needed, just immediately before the insertion of the needle, to pull on the tissues and thus flatten the protruding "cushion" by spreading it out. After the invention the teeth are returned, by a spring for example, to their rest position.

To increase further the precision of the insertion of the needle resulting from using the support base which acts as a front sight for aiming, the hand piece according to the invention can be equipped with magnifying optics not shown in this embodiment but illustrated diagrammatically in FIG. 2 and 3. These optics 60, for example with a sixfold enlargement, can be detachable or stationary.

Now the procedure for using the hand piece just described will be explained.

It will first be assumed that the latter is connected to a central body 20, which will be discussed later, through connection 40: this central body 20 is intended to supply pneumatic, hydraulic and electric energy fluids or others, whose distribution depends on control unit 30, as indicated in the following, which synchronizes, coordinates and sequences the phases of the process.

Syringe 215 has been filled with the appropriate medicinal substance, for example a liquid, and its support 12 has had mounting 52 with its needle 51 attached to it, which in turn is connected, through adapter 53 of its duct section 450, to tip 2153 of the syringe, whose cylinder 2151 is held on body 11. Support 12 of the needle is in rest position, i.e., the tapered or pointed end of the needle is retracted relative to the surface of the claw of support base 14 which is opposite it. Adjustment means 15 (roller wheel 151 of FIG. 2 and 3) are acted on to establish the position of stop 134 to determine the depth of the needle's penetration, which is indicated by slide 152 which moves in front of a scale 153 (FIG. 2 and 3). The quantity and speed of injection of the substance is chosen using a keyboard 311 of panel 31 of control unit 30. The practitioner sets the claw of support base 14 against the epidermis of the area to be treated, using the magnifying optics for aiming if necessary, and presses a release 16. This actuates central body 20 and control unit 30. If needed, pusher 213 pushes the piston of the syringe in a little to purge, if necessary, the air in the duct until a drop of the substance rises from the point of the needle. Then the actuator of the propelling device of the catapult is operated, its piston propelled forward to insert the needle into the patient's tissues, which are stretched between the V-shaped teeth of the claw. It then suffices to wait the chosen period for the injection to be made continuously or in bursts. As will be understood below, the proper progress of the operations and, optionally, indication of any incident which could occur during the process are automatically revealed to the practitioner by control unit 30, which will be discussed below and which includes display screen 312.

For hygienic reasons, a detachable protective hood 141 is placed over the support base and is changed for each patient. This hood can be deformed and extended without rupture when the end base has teeth articulated like scissors handles.

We will now refer to FIG. 2, where another embodiment of a hand piece of the device according to the invention is shown. The same reference numbers will denote similar components.

It will be noted essentially that in this embodiment the hand piece no longer has the dispenser with a syringe and its pusher. The hand piece no longer has the claw of the support base, the needle support and its catapult and, optionally, the detachable magnifying optics. The hand piece is connected to central body 20 by multiple circuit connection 40, to which we will return later.

As can be seen in FIG. 2, the change of configuration of the hand piece makes it possible to reduce its size and weight: by decreasing the moving mass, this allows the elimination or reduction of any recoil and vibration problems which are sources of pain for the patient. In the embodiment diagrammatically shown, the hand piece practically resembles a large, approximately 300 to 700 gram cigar which allows, as can be easily understood, its use even for stomatological procedures.

If necessary, the claw of support base 14 can be adjusted so that the two branches of the V are inclined and no longer remain practically perpendicular to the longitudinal axis of the hand piece. By choosing the angle of inclination of the V of the claw, it is possible to modify the needle's angle of penetration in the patient's tissues and thus to perform tangential insertions.

We will not go any further into the description of this embodiment or the same elements which have the same reference numbers and perform the same functions.

Figure 4:
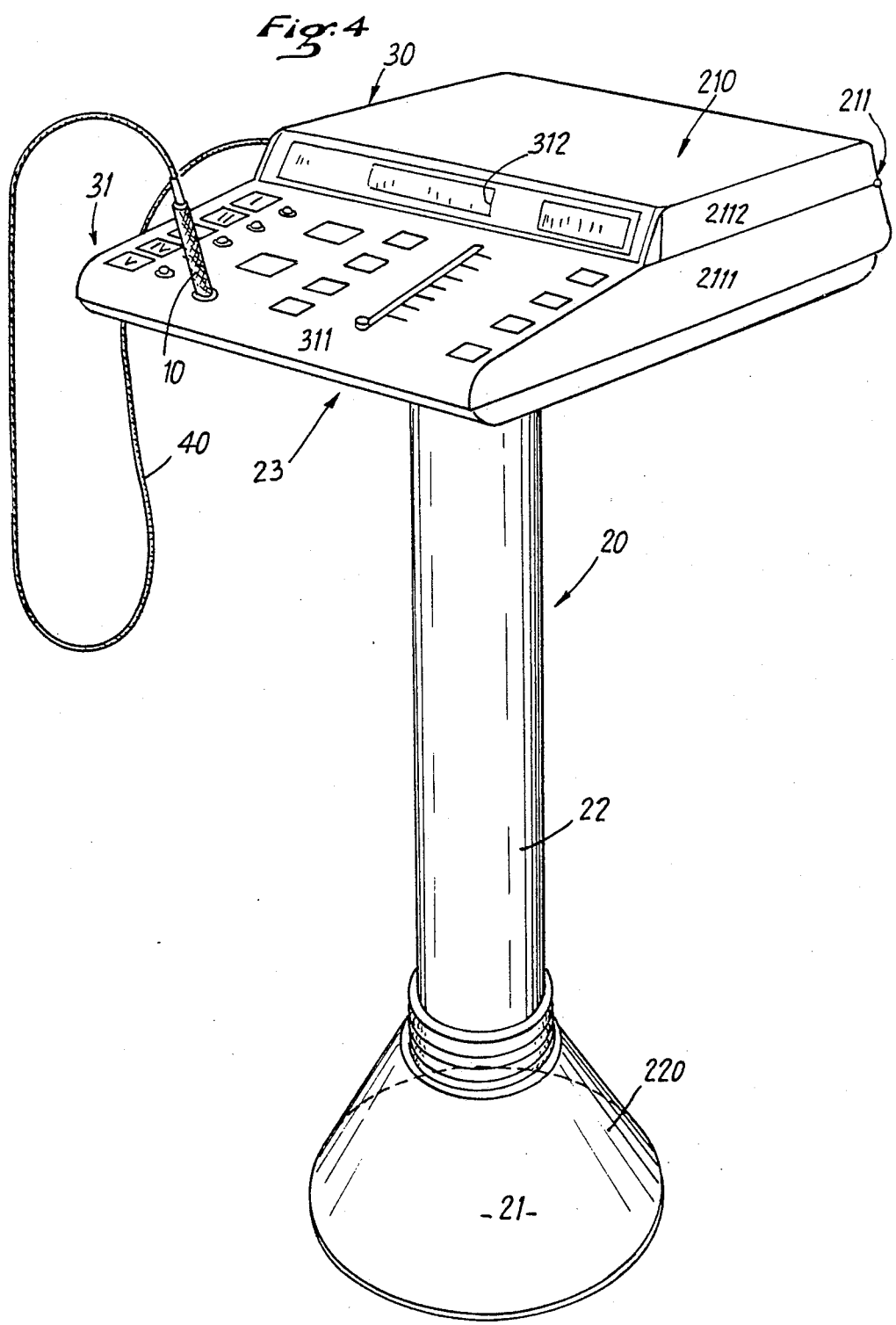
FIG. 4 is a diagrammatic view of the central body and the control unit.

We will now turn to FIG. 4, where central body 20 is basically drawn. This body essentially comprises a base 21, mounted on casters if necessary, on which stands a column 22 which ends in a console 23.

Figure 6:
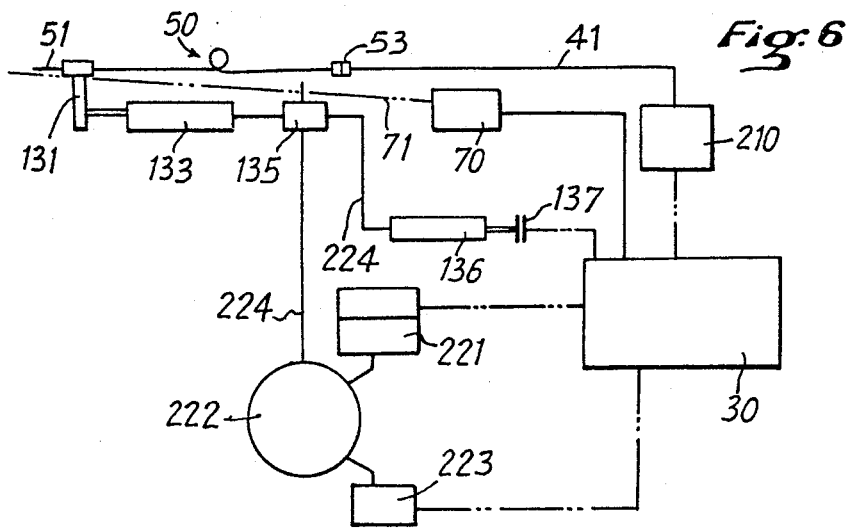
FIG. 6 is a flow sheet of the connections.

The core of the energy fluid supply 220 is located in base 21, i.e., for example, a compressor 221, its tank 222 and all its equipment 223, i.e., the safety valves; the drains; the dust, oil and water filters; the pressure switches and the motor intended to drive it (FIG. 6). All this is standard, we will not go into it further. Console 23, which rests on the upper end of column 22 is in the form of a panel 31 with a keyboard 311 and a display screen 312.

Keyboard 311 is equipped with keys, buttons, cursors or similar devices which allow a choice of the type of injection or sample, i.e., continuous injections or injections in bursts and, in this case, the sequence, duration, frequency and number of impulses of each burst. Likewise, this keyboard allows a choice of the nature of the substance to be injected, the quantity and also the rate of flow. Adjustment means 15 and/or the inclination of the claw to the support base can also be remotely controlled.

The upper part of column 23 which holds dispenser 210 has a compartment 211 which demarcates a chamber 2111, which is closed by a cover 2112 under which are located a receptacle 212 intended to hold various syringes 215 and pushers 213, which are moved by one or more motors 214 to act on piston 2152 of the syringe. The details of the latter are diagrammed in FIG. 5. Cylinder 2151 of the syringes is held on the receptacle using elastic clips or the like to facilitate their exchange.

As is known, the treatment of certain ailments requires the use of injections of various medicinal substances. To do this without it being necessary to make successive insertions of different needles, the device is equipped with single and/or multichannel remote controlled valve(s) (216) which allow a choice of the medicinal substances to be injected and their successive order or mixture following one insertion of a single needle. The medicinal substances to be injected are chosen using the appropriate keys on keyboard 311.

The coordination and sequencing of the proper flow of all the functional operations can easily be adjusted using a programmable microcomputer system, for example, from control unit 30. The manner in which the instructions and the programs are established to make such microcomputers function are well known by experts and do not figure into the framework of the invention. As is known, such coordination and sequencing can also be provided by mechanical or electromechanical means using relays, motors and cams, which is standard.

If necessary, signals indicating the instructions given and the phases during the flow of operations, indicators specifying the components in use and alarm signals showing incidents or failures appear on the display screen 312.

Figure 5:
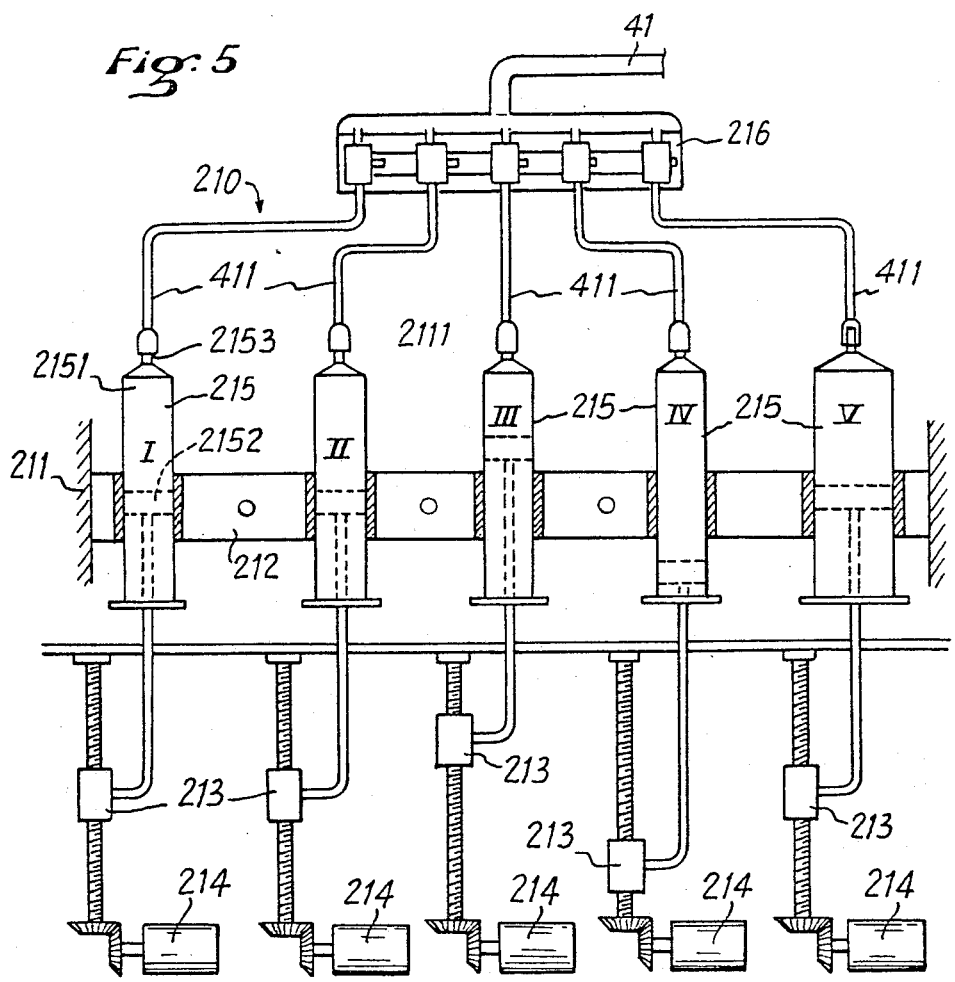
FIG. 5 is a diagrammatic detail view of the console of FIG. 4 showing its dispenser compartment where the syringes are placed.

The manner in which various syringes 215 are mounted in receptacle 212 placed in chamber 2111 of compartment 211 of dispenser 210, which is connected to console 23, is shown diagrammatically in FIG. 5. In this embodiment, the various individual conduits 411 flow into single channel duct 41 through the intervention of remotely controlled valve 216. According to one variant embodiment, duct 41 is multichannel and each of its channels corresponds to a syringe; in such a solution, the end of duct 41 with its channels, to which adapter 53 fits, is in the form of a revolver barrel or the like, for example with as many chambers as channels, the rotation of the barrel being motorized and, if necessary, remotely controlled. For this variant, valve(s) 216 can be eliminated. Multichannel duct 41 is made of a bundle of microcatheters placed side by side or else all in one piece made, for example, by simultaneous extrusion.

It is clear that more syringes intended to contain medicinal substances can be added if necessary, a syringe containing a rinsing product, for example physiological serum, when the duct must be washed because the substances used successively are incompatible or risk reacting and causing incidents for the patient and/or for the device according to the invention. If multichannel duct 41 with several microcatheters is used, allowing for rinsing is no longer of importance because each channel is specialized and the injector is detachable.

As it is standard, the device is equipped at the appropriate places with position and/or travel sensors and with torque or force detectors to make possible, among other things, immediate reaction to any incident or anomaly during functioning which could result from a blockage of a syringe, obstruction of the duct or a plugging up of the needle itself, or any leak in the circuit. Signals representing alarms then appear on the display screen of the panel, along with acoustic signals if necessary. This is standard and there is no reason to go into it further here.

By referring to FIG. 6 it will be understood how the pneumatic as well as electric and hydraulic connections are provided.

Connection 40 includes duct 41, between needle and dispenser, made of a single or multichannel microcatheter, for example: this duct incorporates conduits 411 between syringe and duct, and section 450 between adapter 53 and mounting 52 of the needle. This connection also includes the network and conduits 224, which connect the actuator of propelling device 133 to tank 222 of compressor 221 through its control valve 135 as well as those connecting release 16 to control unit 30. The entire unit is protected by an appropriate flexible casing, for example made of reinforced plastic.

A safety device, consisting for example of an actuator 136 connected to a microswitch, allows dispenser 210 to function only when support 12 has actually been propelled and needle 51 inserted in the tissues.

It will be observed in particular that in the embodiment of the hand piece in FIG. 2 and 3 complete safety is achieved because there is no electric connection or component housed in it.

According to a variant embodiment not illustrated, release 16 of the hand piece controls a low voltage microswitch, according to the safety standards in this field, which acts on one or more appropriate relays.

If necessary a laser 70, He-Ne or IR for example, can be placed in central body 20 and the light impulses can be conveyed using optical fibers 71, which run in or on the hand piece. In such a case, the effects of the medicinal substance can be coupled, by synergism for example, with the action of the photonic impulses delivered by the laser.

Laser techniques and the method of using optical fibers to channel a luminous flux and guide it to a precise point are well known and will not be discussed further. These optical fibers can also be used to drive the luminous flux of a lighting system of the operative field, not illustrated.

As could be noted from reading the description of the device according to the invention and from the way in which the hand piece is used, due to a significant reduction in the size of the moving parts, it is possible to make precise injections or samples with regard to position as well as depth without the least unpleasant effect on the patient, the dexterity of the practitioner playing no role whatsoever.

If necessary, to diminish the unpleasant sensation caused by the penetration of the needle into the patient's tissues, the base of the support can be equipped with a mobile cushioning which is used by coming to strike the tissues, for example between the teeth of the claw, just before the needle propelled by the catapult penetrates the tissues.

The choice of phase difference or time shift between the impact of the cushioning and the penetration of the needle is made according to known physiological data involving sensitive tactile reactions and the thresholds at which they occur. If necessary, to take into account the specific physiological characteristics particular to each patient, a weighting can be provided to lengthen or reduce the duration of this phase difference. To do this, an appropriate button is then placed on the keyboard.

One can thus see the significance of the device according to the invention, which allows precise insertions with regard to position as well as administration of substances or samples by freeing itself from the constraints imposed by the dexterity of the operator.

As was seen, this device can be suitable for general medical use or for specific uses, such as veterinary, as well as for use involving foodstuffs.

In the case of medical use, the device according to the invention allows precise injections in the scalp, for ORL pathologies, treatment of localized hydrolipodystrophies, conjunctive or sclerosing microangiopathies; it also allows treatment of arthrosis of the knee, injections in wrinkles and small wrinkles during dermatoaesthetic interventions, treatment of arthrosis of the fingers, and use in ondotostomatology.

In the preceding it was assumed that the substances, medicinal for example, were liquid fluids but it is clear that, in the absence of contraindications or danger, these fluids can also be gaseous. The architecture of the device is then adapted as a consequence without it being necessary to make any fundamental upheavals; this is within the scope of the expert in the field.

Since the device according to the invention is "reversible" regarding the direction in which dispenser 210 functions, it is clear that the latter can operate to take samples and not make injections. The appropriate changes are easy for an expert.

Use of a pneumatic microactuator to propel the catapult for the device according to the invention results in very high speed needle insertions into the tissues and without the least vibration, due to the very small moving volume and the precision of the guiding. Due to the latter, practically all pain is eliminated and no hematoma is produced, which promotes perfect healing: this is of the utmost importance for wrinkles and small wrinkles.

The depth of the needle's penetration is precisely adjusted using adjustment means which act on the stop; it is clear that these adjustment means can also act on the support base alone or in relation to the stop. Likewise, the operation of the adjustment means can be motorized and be done from the panel.

In the embodiments represented and described it was assumed that the release which triggers operation was located on the hand piece. It is clear that this release can also be located in a pedal appropriately connected to the central body and to the control unit: it can then be operated by foot.

To operate the device according to the invention a compressor driven by a 100-W motor is used, which allows pressures reaching 10 bars to be achieved where only 6 suffice. To supply the catapult a single or multiple conduit, made of a plastic called "Rilsan" and about 6 mm in diameter, is used.

Regarding the duct, one or more microcatheters about 0.6 mm in interior diameter and 2 m in length are used. Medical quality plastic is used and, according to preference, the catheter is not incorporated into the connection so that it remains visible and, if necessary, can easily be changed.

Regarding the dispenser, according to preference 10-cc or 20-cc syringes are used but, for example for those containing rinsing fluid, the capacity can be brought to 20 cc. To obtain maximum flexibility in administering medicinal substances, reversible stepper motors are used to move the pushers. In the same way, the number of drops to be delivered, their specific volume and total, the duration of each drop's production and the frequency of each series of drops and the different series of drops can easily be chosen. A single motor, with suitable transmissions, can also move all the pushers or even only certain ones; if necessary, a specific motor is connected to each pusher. If one motor is used for each pusher and if each individual conduit to a specific syringe is equipped, if necessary, with its own remotely controlled valve, medicinal substances can easily be mixed. It is possible to equip the dispenser with automatic returns for the pushers, for example at the end of travel or at the opening of the dispenser chamber covering cap, to facilitate the exchange or replacement of syringes. The use of electric motors greatly facilitates automation, for example to release the flow of a medicinal substance only after the insertion of the needle or else for keeping track of the rheological characteristics of the various substances which can be stored in the microcomputer, for example. But it is clear that instead of electric motors pneumatic or hydraulic motors or even actuators can be used. Placing the dispenser elsewhere than in the hand piece eliminates the shaking of substances which, in certain cases, are especially fragile and tend to crystallize more or less spontaneously.

Finally it will be noted that the central body and the control unit can also be located in one or more suitcases to facilitate transport and thus allow ambulatory treatment or treatment at home.

To facilitate management, the device can be equipped with an appropriate meter connected, for example, to the console, to count the number and the nature of interventions and the quantities of substances used.

We claim:

1. A device for injecting or withdrawing substances in an environment, particularly in the tissues of living beings, comprising at least one dispenser for said substance and a hand piece for holding an injector, said injector comprising an adaptor for connection thereof to said dispenser, a support for removably supporting a needle, a flexible conduit extending between said adaptor and said support for feeding said needle with said substance, whereby said needle support may move independently of said dispenser, means defining a guide path for movement therealong of said support between a rest position and an active position, catapult means for propelling said support from its rest position to its active position, and a support base for engaging a surface of said environment, said device further comprising pumping means for pumping said substance from said dispenser to said needle, and control means for controlling said pumping means and said catapult means.

2. A device according to claim 1, wherein said catapult means comprises a propelling device including a pneumatic actuator and wherein said body comprises a supply of motive fluid and a remotely controlled valve operated by said control means.

3. A device according to claim 2, wherein the dispenser comprises plural syringes, each comprising a cylinder and a piston therein, all of said cylinders being connected in parallel by respective conduits to a duct, and wherein the remotely controlled valve comprises a multichannel solenoid disposed in the conduit between said syringes and said support.

4. A device according to claim 3, wherein said duct is multichannel and has as many channels as there are syringes.

5. A device according to claim 1, further comprising a carriage, said support being mounted upron said carriage, and a plurality of adjustable slides defining said guide path, said carriage being movable upon said slides.

6. A device according to claim 1, wherein said support base is in the form of a vee in the path of the needle, through which the needle passes.

7. A device according to claim 1, further comprising adjustment means for determining the distance the needle projects with respect to the support base when in its active position.

8. A device according to claim 7, further comprising a stop against which the adjustment means act.

9. A device according to claim 7, wherein the adjustment means controls the position of the support base.

10. A device according to claim 1, wherein the dispenser comprises at least one syringe, each syringe comprising a piston and a cylinder connected to a duct via a conduit, a pusher to act on the piston of the syringe, a motor for moving the pusher, and a remotely controlled valve located between the syringe and said support.

11. A device according to claim 10, wherein the motor is a variable speed motor.

12. A device according to claim 10, wherein the motor is reversible.

13. A device according to claim 1, wherein one of said syringes contains a rinsing fluid.

14. A device according to claim 1, wherein said control means comprises a programmable microcomputer.

15. A device according to claim 1, wherein said connection further comprises a conduit to supply the catapult.

16. A device according to claim 1, wherein said connection is non-electric.

17. A device according to claim 1, further comprising a release to trigger operation of the device.

18. A device according to claim 17, wherein said release is on said hand piece.

19. A device according to claim 1, wherein said release is triggered by a pedal on a central unit.

20. A device according to claim 1, wherein said needle is rigidly affixed to a mounting on said injector.

21. A device according to claim 1, wherein said mounting is connected to a duct section having an adapter.

22. A device according to claim 1, wherein said hand piece further comprises a cushion.

23. A device according to claim 1, wherein the dispenser comprises a syringe and a pusher carried by the hand piece.

* * * * *